(12) United States Patent
Lennernäs et al.

(10) Patent No.: US 8,999,389 B2
(45) Date of Patent: Apr. 7, 2015

(54) BIORESORBABLE CONTROLLED-RELEASE COMPOSITION

(75) Inventors: Hans Lennernäs, Uppsala (SE); Niklas Axén, Järlåsa (SE)

(73) Assignee: Lidds AB, Helsingborg (SE)

( * ) Notice: Subject to any disclaimer, the term of this patent is extended or adjusted under 35 U.S.C. 154(b) by 704 days.

(21) Appl. No.: 12/224,942

(22) PCT Filed: Mar. 14, 2007

(86) PCT No.: PCT/EP2007/002250
§ 371 (c)(1),
(2), (4) Date: Nov. 5, 2008

(87) PCT Pub. No.: WO2007/104549
PCT Pub. Date: Sep. 20, 2007

(65) Prior Publication Data
US 2009/0118215 A1      May 7, 2009

(30) Foreign Application Priority Data
Mar. 14, 2006   (DK) .................................. 2006 00361

(51) Int. Cl.
*A61K 9/00*     (2006.01)
*A61K 9/16*     (2006.01)

(52) U.S. Cl.
CPC ............. *A61K 9/0024* (2013.01); *A61K 9/0034* (2013.01); *A61K 9/1611* (2013.01); *A61K 9/1694* (2013.01)

(58) Field of Classification Search
None
See application file for complete search history.

(56) References Cited

U.S. PATENT DOCUMENTS

| | | | |
|---|---|---|---|
| 3,797,758 A * | 3/1974 | Cherdron et al. ............... | 241/29 |
| 5,318,779 A | 6/1994 | Hakamatsuka et al. | |
| 6,030,636 A * | 2/2000 | Randolph et al. ............. | 424/426 |
| 6,391,336 B1 | 5/2002 | Royer | |
| 6,544,290 B1 | 4/2003 | Lee et al. | |
| 6,630,486 B1 | 10/2003 | Royer | |
| 6,972,130 B1 | 12/2005 | Lee et al. | |
| 2002/0155144 A1 | 10/2002 | Troczynski et al. | |
| 2003/0082232 A1 | 5/2003 | Lee et al. | |
| 2003/0170307 A1 | 9/2003 | Royer | |
| 2003/0215484 A1* | 11/2003 | Axen et al. ..................... | 424/423 |
| 2004/0265350 A1 | 12/2004 | Sambrook et al. | |

FOREIGN PATENT DOCUMENTS

| EP | 0376331 A | 7/1990 |
|---|---|---|
| WO | WO05/039537 | 5/2005 |

OTHER PUBLICATIONS

Majling, J., et al., Mat. Res. Soc. Symp. Proc., vol. 114, 1988, pp. 285-288.*
Svenska Keraminstitutet, Freeze Granulation, pp. 1-16, date available: Jan. 19, 2004.*
H. Gauthier et al., "Influence of isostatic compression on the stability of vancomycin loaded with a calcium phosphate-implantable drug delivery device", © 2000 John Wiley & Sons, Inc.

* cited by examiner

*Primary Examiner* — Scott Long
*Assistant Examiner* — Lyndsey Beckhardt
(74) *Attorney, Agent, or Firm* — Sterne, Kessler, Goldstein & Fox P.L.L.C.

(57) ABSTRACT

A novel method for the preparation of a highly densified and at least partly, preferably fully or almost fully hydrated ceramic for use in the preparation of a pharmaceutical composition notably for controlled-release of one or more therapeutically, prophylactically and/or diagnostically active substance. The method involves a concomitant step of hydrating and densifying a bioresorbable and hydratable ceramic such as calcium sulphate. The invention also relates to compositions comprising such a highly densified ceramic. The pharmaceutical composition is useful for targeted and controlled local prolonged release of active substances, e.g. anti-cancer agents, whereby the spectrum and severity of side effects are minimized due to an optimized local concentration-time profile.

46 Claims, 7 Drawing Sheets

(a)

(b)

BIORESORBABLE CONTROLLED-RELEASE COMPOSITION

FIELD OF THE INVENTION

Figure 1:
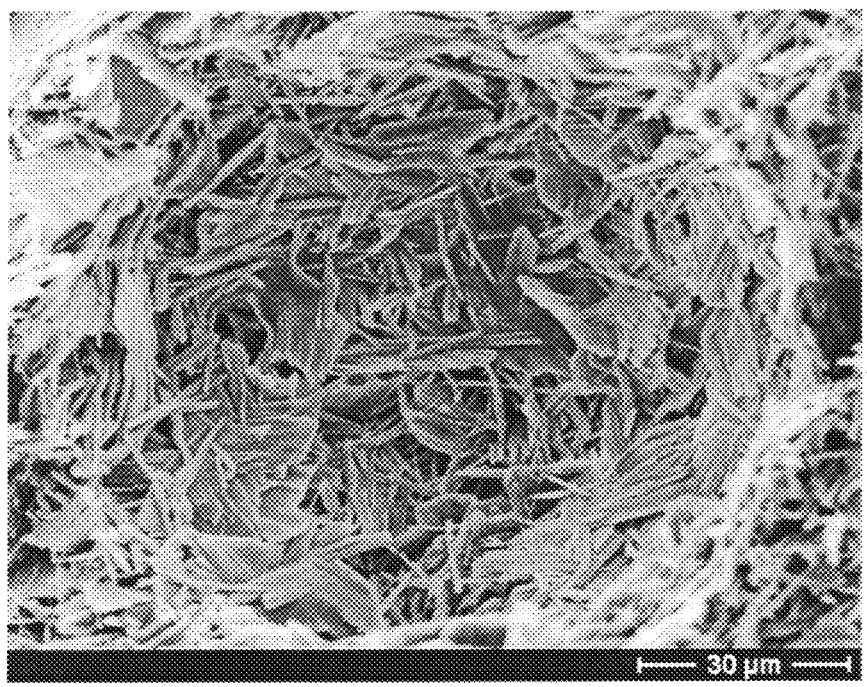
Figure 1:
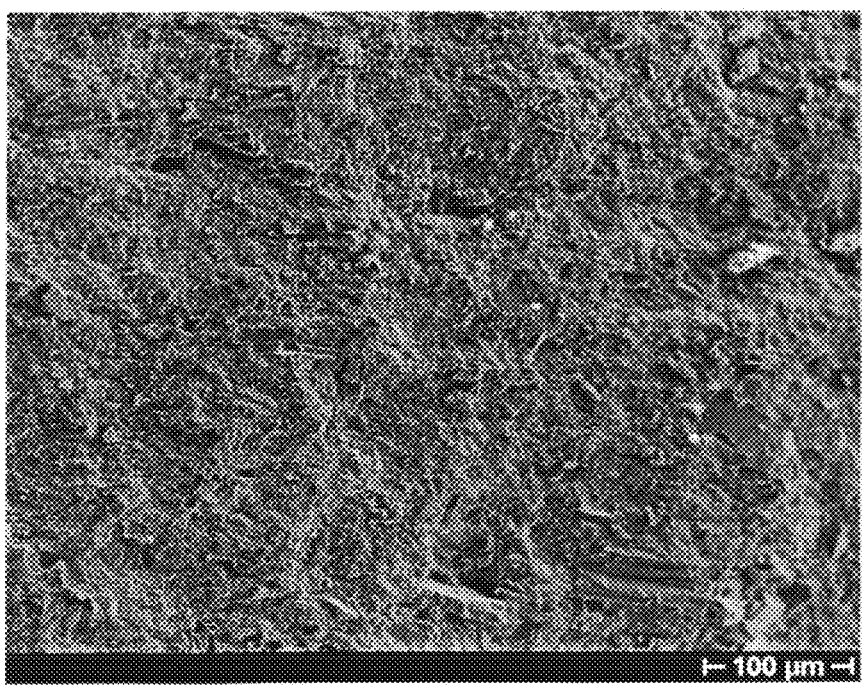

The present invention relates to a novel method for the preparation of a highly densified and at least partly, preferably fully or almost fully hydrated ceramic for use in the preparation of a pharmaceutical composition notably for controlled-release of one or more therapeutically, prophylactically and/or diagnostically active substance. The method involves a concomitant step of hydrating and densifying a bioresorbable and hydratable ceramic. The invention also relates to compositions comprising such a highly densified ceramic. The pharmaceutical composition is useful for targeted and controlled local prolonged release of active substances, e.g. anti-cancer agents, whereby the spectrum and severity of side effects are minimized due to an optimized local concentration-time profile.

BACKGROUND OF THE INVENTION

A range of drug delivery systems for local, controlled and/or targeted delivery therapy has been developed in the past. Many are based on bioresorbable (or biodegradable) polymers, bioresorbable ceramics and/or hydrogel(s) as carriers for the therapeutically active substance. Commonly used biodegradable polymers are polylactic acids and polylactic-co-glycolide-acids. Various calcium-salt based ceramics, e.g. calcium phosphate or calcium sulphate systems, or hydroxy-lapatite, have been described in the form of beads, granules, scaffolds or moldable pastes, to carry and release drugs in both active and inactive form, e.g. hormones, antibiotics, antiviral, anticancer, analgesic, anticoagulant and bone growth factors to surrounding tissues. These ceramics are often referred to as hydratable or hydrating ceramics due to their ability to react chemically with water to form hydrates. See e.g. Royer U.S. Pat. No. 6,391,336, U.S. Pat. No. 6,630,486, US 2003/0170307.

When bioresorbable (or biodegradable) and hydratable ceramic carriers are used, the release mechanisms rely on the inherent properties of the hydratable ceramic materials after solidification through hydration. For example, calcium sulphate in the form of its hemi-hydrate rapidly binds additional water and forms the calcium-sulphate di-hydrate. When a mixture of ceramic powder and active drug is exposed to water and hydrates, the active drug or prodrug is bound into a matrix/carrier of the hydrated material. Due to a combination of factors such as the limited amount of water possible to bind in the hydration reactions, limiting the possible amount of hydrate phases being formed to fill the gaps between powder grains, and the necessity for at least some water transport for the hydration to proceed, some degree of porosity remains after hydration. The porosity formed as a result of normal hydration is often referred to as the residual micro-porosity. After a normal hydration of calcium sulphate hemi-hydrate the micro-porosity constitutes about 30-50 vol. %. In an in vivo situation, the active drug or prodrug is released from the carrier, entering the surroundings, by mechanisms involving e.g. diffusion through the pore system and/or erosion of the carrier material.

Ceramic substances as e.g. calcium sulphate have been suggested as implant materials for controlled release of active substances (see e.g. Royer U.S. Pat. No. 6,391,336, U.S. Pat. No. 6,630,486, US 2003/0170307). In order to obtain a slower and controlled release of the active substance(s) from the ceramics, Royer uses a complexing agent that is a polymeric substance that forms a complex with the active substance, whereby a slower drug release may be obtained.

The bioresorbable ceramics have many favorable properties for pharmaceutical formulations in controlled release applications as compared to polymers, such as biocompatibility and biodegradability. In general, the bioresorbable ceramics are non-toxic and are based on molecules which normally occurring in the living tissues of mammals. Calcium sulphate is particularly attractive since it is a resorbable and biocompatible material, i.e. it disappears over time.

However, the release rate of therapeutic substances from ceramic carriers has turned out to be difficult to control. For both calcium phosphate and calcium sulphate based ceramic systems, the release rate is too high for a long-term drug delivery system. Furthermore, in some cases formulations are desired, which offer a combination of an immediate and/or rapid boost-like therapeutic dose in combination with a slower and controlled release dosing over a prolonged period of time.

The PCT-application WO 05/039537 discloses a pharmaceutical composition comprising a bioresorbable hydratable ceramic, sorbed aqueous medium, and an active substance. In the described composition the release rate is controlled by sealing the porosity.

This invention offers a technique to reduce and control the drug release rate of a bioresorbable and hydratable ceramic when used as a carrier for therapeutic agents. With the invention also combinations of more rapid release and slower release characteristics in the same pharmaceutical formulation can be achieved.

SUMMARY OF THE INVENTION

The present invention provides in a first aspect, a method for the preparation of a highly densified and at least partly hydrated ceramic. In specific embodiments, the ceramic obtained by the method is fully or almost fully hydrated. The method involves subjecting one or more hydratable and bioresorbable ceramics to a process which involves hydrating the ceramic under an external pressure. The hydration is a chemical process, e.g. in the case of calcium sulphate, the hydration transform calcium sulphate hemi-hydrate to calcium sulphate di-hydrate. The process is normally initiated by adding at the most a molar equivalent amount of water (notably in the form of an aqueous medium optionally comprising one or more additives) to the ceramic in powder or crystal form. However, as described herein, additives may be added to the aqueous medium that delays the onset of the hydration process and/or the duration of the hydration process, and, accordingly, the time to cure the ceramic. Dependent on the apparatus used to provide the external pressure, the water can be added before (e.g. up to several hours before) or immediate before subjecting the ceramic to the external pressure or, if the apparatus is designed thereto, during application of the external pressure.

Hydratable ceramics have the ability to bind water and form water-rich crystals. When water is added to a powder of a hydratable ceramic, the powder grains transforms to a new crystal form richer in water. This hydration reaction, which is a recrystallisation, often results in a solidification of the powder-water mix to a solid material. The rate of hydration as well as the water absorption capability varies depending on the type hydrating ceramics as well as on system parameters such as grain size, temperature, pH-value, etc. The starting ceramic may be water-free or in a semi-hydrated form. Some ceramics form intermediate hydrates in-between the water free and the fully hydrated form. For each hydratable ceramic there is also a defined fully hydrated form which cannot bind additional water. For the particularly interesting case of calcium sulphate, there is a water free anhydrous form, an intermediate hydrate with 0.5 units of water per unit of calcium sulphate, and the fully hydrated calcium sulphate di-hydrate with 2 units of water per unit of calcium sulphate.

In another aspect, the invention relates to a pharmaceutical composition comprising one or more hydratable and bioresorbable ceramics and one or more therapeutically, prophylactically and/or diagnostically active substances, wherein the one or more active substances are at least partly present in a ceramic that is highly densified and at least partly hydrated.

A pharmaceutical composition according to the invention is intended to release the active substance during a prolonged period of time, notably during at least 3 days or more such as, e.g. at least 5 days, at least 1 week, at least 2 weeks, at least 3 weeks, at least 1 month, at least 2 months, at least 3 months or at least 6 months.

DETAILED DESCRIPTION OF THE INVENTION

The present inventors have found that the drug release rate of a pharmaceutical composition, based on a ceramic carrier, may be adjusted and reduced by subjecting a ceramic comprising an active substance to densification and hydration in several steps. The densification of the ceramic is achieved by subjecting a ceramic composition to an external pressure, the densification may optionally further be optimized by an at least partly hydration, i.e. a reaction with water to form calcium sulphate di-hydrate (in the case of calcium sulphate as ceramic), during the applied pressure. In a specific embodiment almost fully hydration is achieved during the densification step. Hydration during densification is advantageous with respect to delay of release of the active substance, cf. the examples herein. Both the pressure controlled densification and hydration contribute to the formation of a highly densified structure, which better entraps one or more active substance(s) and hereby reduces the drug release rate.

A Pharmaceutical Composition for Controlled Release

In an aspect the present invention relates to a pharmaceutical composition comprising one or more hydratable and bioresorbable ceramics and one or more therapeutically, prophylactically and/or diagnostically active substances, wherein the active substances are at least partly present in a ceramic that is highly densified and at least partly hydrated.

By the term "a highly densified ceramic" is referred to a ceramic which has been subjected to a pressure, an externally applied pressure, e.g. a compression, optionally in combination with an at least partly hydration under external pressure, whereby the pore size and the porosity of the at least partly hydrated ceramic are decreased leading to a highly densified structure of the ceramic. By the present method, densification is carried out at the same time as the hydration of the ceramic takes place in order to obtain a highly densified structure. The highly densified structure obtained (exemplified with calcium sulphate) is characterized by a typical pore size of at the most about 100 nm such as, e.g., at the most about 75 nm, at the most about 50 nm or at the most about 10 nm; and a porosity of at the most about 10% such as, e.g., at the most about 5%, at the most about 3%, at the most about 2% or at the most about 1%. For example, a hydration under applied pressure of at least 100 MPa, and preferably of 200 MPa or more, reduces the porosity to below 10% and reduces the pore size to below 100 nm.

According to the invention, several techniques may be used to apply the external pressure, for example uniaxial pressing or isostatic pressing (hot or cold). Cold Isostatic Pressing (CIP), applied to preformed bodies of calcium sulphate containing the selected active components, has been found to be an effective method to produce highly densified and homogenous bodies. For an optimal densification, the ceramic bodies may be covered with e.g. a capsule (e.g. an elastic balloon) during pressurising. Normally, the applied pressure should be at least 50 MPa such as, e.g., at least 100 MPa, at least about 200 MPa, preferably 300 MPa or above. However, the pressure required is dependent on the pressing apparatus employed. Thus, the above-mentioned pressures are suitable for use in case of CIP, whereas in the case of e.g. a uniform uniaxial pressing, pressures are normally applied that are higher such as, e.g., at the most about 200 MPa, preferably about 300 MPa or more, about 400 MPa or more, or about 500 MPa or more.

In one embodiment of the invention, the highly densified ceramic has been subjected to an external pressure or compression. A suitable pressure is of at least 100 MPa and preferably of at least 200 MPa or above such as at least 300 MPa.

As seen from the examples herein the highly densified and at least partly hydrated ceramic may be partly or fully hydrated during employment of external pressure and/or— in the case of partly hydration during densification, it may be subjected to fully or almost fully hydration after employment of external pressure.

In the present context the term "hydration" refers to the chemical process of transforming e.g. calcium sulphate hemihydrate to calcium sulphate dihydrate. The hydration process is typically started by adding an aqueous medium to the calcium sulphate hemi-hydrate and dependent on the amount of water added and the amount of calcium sulphate hemihydrate, the calcium sulphate may be partly or fully hydrated. In the present context, the term "partly hydrated" is intended to denote a ceramic, wherein the amount of aqueous medium added corresponds to at least about 20% of the stoichiometric amount necessary to hydrate the one or more hydratable and bioresorbable ceramics, whereas the term "fully hydrated" is intended to denote a ceramic, wherein the amount of aqueous medium added corresponds to at least 90%, at least 95% or at least 99%, notably 100% of the stoichiometric amount necessary to hydrate the one or more hydratable and bioresorbable ceramics.

In the present context, the term "bioresorbable" is intended to denote a material that can be dissolved and/or degraded in body fluids or organs or otherwise eliminated by the human body.

In one embodiment the one or more hydratable and bioresorbable ceramics has—e.g. when subjected to external pressure of at least 100 MPa—a porosity of at the most about 10% such as, e.g., at the most about 5%, at the most about 3%, at the most about 2% or at the most about 1%.

The term porosity, or micro-porosity, refers to micron sized pores distributed within the material. This type of porosity can be measured e.g. by comparing the density of a certain body to that of an ideally dense body, or by measuring the density increase caused by infiltration of the pores by a medium of known specific weight, or by using a method such as the Hg porosity measurement method (e.g. Micromeritics AutoPore III 9410), or by using microscopy.

The inventors have found that the application of an external pressure to a mixture of ceramic powder, active substance(s) and sorbed aqueous medium, produces a more favorable micro-structure characterized by low porosity and a pore network which is narrower in its dimensions. Alternatively, the mixture of ceramic powder and active substance(s) may be subjected to a first step in which the mixture is compressed by use of a lower compression, e.g. at 20 MPa, followed by a second step at a higher pressure, such as at least 100 MPa. The hydration typically takes place during application of the higher pressure (i.e. normally not during the compression with a lower pressure). This lower porosity reduces the drug release rate of active and/or prodrug substance(s) embedded in the highly densified microstructure. It is believed that the drug release from a densified structure takes place predominantly via erosion and/or resorption/dissolution of the overall pharmaceutical composition rather than by leaching through the implant porosity. The smaller the pore size and the more reduced the porosity, the less release of the active substance is expected to occur by diffusion of the active and prodrug substance(s) from the ceramic carrier. A highly densified ceramic (exemplified by calcium sulphate) is characterized by a typical pore size of at the most about 100 nm such as, e.g., at the most about 75 nm, at the most about 50 nm or at the most about 10 nm; and a porosity of at the most about 10% such as, e.g., at the most about 5%, at the most about 3%, at the most about 2% or at the most about 1%. For example, a hydration under applied pressure of at least 100 MPa, and preferably of 200 MPa or more, reduces the porosity to below 10% and reduces the pore size to below 100 nm. It is contemplated that deviations in the figures stated above may be of relevance dependent on the ceramic in question.

According to the invention, the one or more bioresorbable hydratable ceramics may be chosen from several bioresorbable and biocompatible hydratable ceramics, the ceramic may be non-hydrated, hydrated, i.e. fully hydrated, semi-hydrated or partly hydrated. Suitable hydratable ceramics for use in a composition according to the invention may be selected from the group consisting of calcium sulphate such as, e.g., α-calcium sulphate, β-calcium sulphate; calcium sulphate hemi-hydrate; calcium sulphate di-hydrate; calcium phosphate; calcium carbonate; calcium fluoride; calcium silicate; magnesium sulphate; magnesium phosphate; magnesium carbonate; magnesium fluoride; magnesium silicate; barium sulphate; barium phosphate; barium carbonate; barium fluoride; and barium silicate; and mixtures thereof. Any combination of these ceramics is of relevance to the invention.

In a preferred embodiment of the invention the one or more bioresorbable and hydratable ceramics is non-hydrated, hydrated, semi-hydrated or partly hydrated calcium sulphate such as for example α-calcium sulphate, β-calcium sulphate, or calcium sulphate hemi-hydrate, or calcium sulphate di-hydrate.

Furthermore, as will appear from the below described method of densifying a bioresorable and hydratable ceramic and the detailed examples, the densification, and hereby the reduction of the drug release rate, may further be enhanced by several possible procedures. For example, the effect of pressure is improved if the starting ceramic powder has a fine grain size, preferably below 10 microns, such as the most about 8 μm, the most about 7 μm, the most about 6 μm or the most about 4 μm. Accordingly, in one preferred embodiment of the invention, prior to the densification the bioresorable and hydratable ceramic employed in the preparation of the highly densified ceramic is milled, producing a mean particle size of at the most about 10 μm. In another preferred embodiment of the invention the bioresorable and hydratable ceramic employed in the preparation of the highly densified ceramic part is both milled and granulated, such as by a freeze granulation procedure. Other granulation processes suitable for use are e.g. wet granulation or dry granulation.

According to the present invention the total amount of water used to hydrate the one or more ceramics preferably corresponds to the stoichiometric amount necessary to fully or almost fully hydrate the one or more bioresorable and hydratable ceramics. Alternatively, the total amount of water in the highly densified one or more ceramics corresponds to at least about 50% of the stoichiometric amount necessary to hydrate the one or more hydratable and bioresorbable ceramics, such as at least 75%, at least 80%, at least 85%, at least 90%, at least 95% or at least 99%.

However, the inventors have surprisingly found that by adding the aqueous medium in a one or two step procedure to obtain a one or two step hydration improves the densification further. The one step procedure involves addition of the aqueous medium before the densification, whereas the two step procedure typically involves addition of a part of the aqueous medium before or during the densification, and another part added after the pressurizing step, then the densification is further improved. Accordingly, an optimized densification effect is achieved by pressurising a preformed body of e.g. calcium sulphate with a less than stoichiometric amount of aqueous medium (e.g. less water than what is bonded in an ideal full hydration). The remaining aqueous medium is favourably added in a post-hydration step after removal of the pressure. It is hypothesised that a more than stoichiometric, or even a stoichiometric, amount of e.g. water leads to pockets of free, non-bonded, water not taking part in the hydration preventing an ideal densification. In a specific embodiment of the invention the amount of aqueous medium added to a ceramic prior to or during a densification is a less than stoichiometric amount, and the remaining aqueous medium is added in a post-hydration step after the initial densification to allow a full hydration. In the present context the term "post-hydrating" is used to describe the addition of water after the densification step, i.e. a further hydration takes place after the high pressure densification procedure.

In a specific embodiment of the invention, the starting material for the manufacture of the bioresorable and hydratable ceramic is calcium sulfate hemi-hydrate and the total amount of sorbed aqueous medium is at the most 1.5±0.015 equivalents of water. Calcium sulphate hemi-hydrate crystals contains 0.5 mol water per 1.0 mol calcium sulphate, for a full hydration, i.e. formation of calcium sulphate di-hydrate, additional 1.5 mol water is therefore needed.

The composition of the invention may be in the form of rods, cylinders, tablets, beads or in a particulate form. In some embodiments the composition is intended to be admixed with an aqueous medium prior to administration. Such a composition may be designed to cure in situ after in vivo administration.

The one or more therapeutically, prophylactically and/or diagnostically active substances may be dispersed (including homogeneously dispersed) in the highly densified and at least partly hydrated ceramic, or the ceramic may wholly or at least partly encapsulated the one or more therapeutically, prophylactically and/or diagnostically active substances.

In a pharmaceutical composition according to the present invention, the one or more therapeutically, prophylactically and/or diagnostically active substances are homogeneously dispersed in the highly densified ceramic. The drug load of said active substance in the densified ceramic is at the most about 50% w/w, such as e.g. at the most 40% w/w, at the most 35% w/w, at the most 25% w/w, at the most 20% w/w.

As described in the prior art, a micro-porosity can be partly sealed with pharmaceutical additives of hydrophobic character. The inventors of the present invention have surprisingly found, that the one or more drug substance, contained in a composition according to the invention, in itself may reduce its own release rate. As it can be seen from the examples below, an increased drug load gave surprisingly a significantly lower release rate. A possible hypothesis for this effect may be that the drug substance function as a hydrophobic agent, partly sealing the micro-porosity. For example, by changing the amount of active substance from 50 mg 2-hydroxyflutamide per g calcium sulphate hemi-hydrate (5 w/w %) to 100 mg per g calcium sulphate hemi-hydrate (10 w/w %) the release rate is controlled over a more prolonged time-period. Accordingly, in a preferred embodiment of the invention the drug load of the one or more therapeutically, prophylactically and/or diagnostically active substances is at the most about 50% w/w, such as e.g. at the most 40% w/w, at the most 35% w/w, at the most 25% w/w, at the most 20% w/w.

The pharmaceutical composition according to the invention, are applicable with any therapeutically, prophylactically and/or diagnostically active substances that may require a controlled release, especially a prolonged controlled release. Examples of relevant pharmacological classes are e.g. anti-cancer agents. With regard to anti-cancer agents, i.e. neoplastic agents, the invention may be used for targeted and controlled local release of hormonal, anti-hormonal, chemotherapeutic and/or other pharmacological agent(s).

In a preferred embodiment of the invention, the one or more therapeutically, prophylactically and/or diagnostically active substances in the highly densified ceramic are suitable for use in prostate related diseases or conditions. Furthermore, in a more specific embodiment of the invention, the active substance is an androgen or a derivative thereof, an anti-androgen or a derivative thereof, an oestrogen or a derivative thereof, an anti-oestrogen or a derivative thereof, a gestagen or a derivative thereof, an anti-gestagen or a derivative thereof, an oligonucleotide, a progestagen or a derivative thereof, a gonadotropin-releasing hormone or an analogue or derivative thereof, a gonadotropin inhibitor or a derivative thereof, an adrenal and/or prostate enzyme inhibitor, a membrane efflux and/or membrane transport protein, an immune system modulator, an angiogenesis inhibitor, or combinations thereof.

A composition of the invention may also include any other suitable active substance suitable for application in soft tissues or organs for local or systemic sustained drug release. The sustained drug release compositions of the invention can also be explored in other treatments e.g.: pain, neurological diseases (Alzheimer, Parkinson), autoimmune diseases, immunological diseases, and diseases responding to immunological and immunomodulating therapy (hepatitis, MS, tumours), infections, inflammations, metabolic diseases, obesitas, diseases in the uro-genital tract, cardiovascular diseases (including blood pressure), hematopoietic, anticoagulant, thrombolytic and antiplatelet diseases, chemotherapy of parasitic infections, microbial diseases and neoplastic diseases, hypercholesterolemia, dyslipidemia, hematopoetic diseases, respiratory diseases (asthma, chronical lung obstruction), diseases of the kidney, gastrointestinal diseases, liver diseases, hormonal disruption, replacement and substitution, vitamins replacement and substitution. Examples of active substances from various pharmacological classes for the use in the present clinical context include e.g. antibacterial agents, antihistamines and decongestants, anti-inflammatory agents, antiparasitics, antivirals, local anaesthetics, antifungals, amoebicidals or trichomonocidal agents, analgesics, antianxiety agents, anticlotting agents, antiarthritics, antiasthmatics, anticoagulants, anticonvulsants, antidepressants, antidiabetics, antiglaucoma agents, antimalarials, antimicrobials, antineoplastics, antiobesity agents, antipsychotics, antihypertensives, auto-immune disorder agents, anti-impotence agents, anti-Parkinsonism agents, anti-Alzheimers agents, antipyretics, anticholinergics, anti-ulcer agents, anorexics, beta-blockers, beta-2 agonists, alpha receptor antagonists and agonists, blood glucose-lowering agents, bronchodilators, agents with effect on the central nervous system, cardiovascular agents, cognitive enhancers, contraceptives, cholesterol-reducing agents, agents against dyslipidemia, cytostatics, diuretics, germicidals, H-2 blockers, hormonal agents, anti-hormonal agents, hypnotic agents, inotropics, muscle relaxants, muscle contractants, physic energizers, sedatives, sympathomimetics, vasodilators, vasoconstrictors, tranquilizers, electrolyte supplements, vitamins, uricosurics, cardiac glycosides, membrane efflux inhibitors, membrane transport protein inhibitors, expectorants, purgatives, contrast materials, radiopharmaceuticals, imaging agents, peptides, enzymes, growth factors, vaccines, mineral trace elements, etc.

The therapeutically, prophylactically and/or diagnostically active drug substance(s) may also be in the form of a pharmaceutically acceptable salt, solvate or complex thereof or in any suitable crystalline or amorphous form or in the form of a prodrug.

In a specific embodiment the active substance is one or more cytostatics such as one or more alkylating agents, one or more antimetabolites, one or more antimitotics, one or more topoisomerase inhibitors, one or more biological cytoregulators, one or more hormone or antihormones and the like.

More specifically, the one or more active substance may be an alkylating agent like e.g. mephalan, busulfan, carboplatin, cisplatin, cyclophosphamid, dacarbazin, chlorambucil, lomustin, carboplatin, temozolomid, treosulfan;

an antimetabolite like e.g. pemetrexed, cytarabin, azathioprin, fludarabinphosphat, fluoruracil, hydroxyurea, cladribin, methotrexat, tegafur, uracil, capecitabin;

an antimicotics like e.g. vinorelbin, vinkristin, pacitaxel, docetaxel, vinblastin;

a topoisomerase inhibitor like e.g. doxorubicin, amsakrin, irinotecan, daunorubicin, epirubicin, etoposid, idarubicin, topotecan, mitomycin, mitoxantron;

a biological cytoregulator like e.g. bleomycin;

a hormone or antihormone like e.g. polyestradiolphosphate, estradiol, anastrozol, exemestan, fluvestrant, letrozol, tamoxifen, megestrolacetate, medroxyprogesteron acetate, octreotid, triptorelin, leuprorelin, buserelin, goserelin;

asparaginase;

tyrosinkinase inhibitor like e.g. imatinib other agents like e.g. mitotan, celecoxib, lenograstim, interferon γ-1b, interferon α-2b, pegfilgrastim, filgrastim, aldesleukin, bevacizumab, cetuximab, trastuzumab, alemtuzumab, rituximab, bortezomib, temoporfin, methylaminolevulinat, anagrelid, estramustinphosphat.

In a preferred aspect, the active substance is suitable for the treatment of prostate related diseases or conditions including those mentioned herein below.

In a specific embodiment of particular interest, the composition of the invention is suitable for use in the treatment of prostate diseases, more specifically benign prostatic hyperplasia, prostate cancer and/or prostatitis. For the treatment of prostate related diseases is may be especially useful to use anti-cancer agents such specific anti-androgens. In a more preferred embodiment of the invention, the one or more therapeutically, prophylactically and/or diagnostically active substances are flutamide, hydroxy-flutamide, cyproteron, nilutamide or bicalutamide or the like. Additionally, in some cases it may be favorable to use a combination of an anti-androgen and a gonadotropin-releasing hormone or an analogue thereof.

The compositions of the invention, including the active substance (s), can be applied locally with minimally invasive techniques, and a sustained (controlled) local release profile of the drug over a prolonged period of time can be obtained. Such local and sustained delivery of active substances optimises the local concentration-time profile of the active substances and their local pharmacological effects, and minimises the systemic exposure and thus reduces the side-effects, and hence increases the safety and utility of the active substance and the pharmaceutical composition containing the active substance. In addition the compliance of the therapy is enhanced.

In another embodiment of the invention, the therapeutically, prophylactically and/or diagnostically active substance in the highly densified ceramic is an androgen or a derivative thereof, an anti-androgen or a derivative thereof, an oestrogen or a derivative thereof, an anti-oestrogen or a derivative thereof, a gestagen or a derivative thereof, an anti-gestagen or a derivative thereof, an oligonucleotide, a progestagen or a derivative thereof, a gonadotropin-releasing hormone or an analogue or derivative thereof, a gonadotropin inhibitor or a derivative thereof, an adrenal and/or prostate enzyme inhibitor, a membrane efflux and/or membrane transport protein, an immune system modulator, an angiogenesis inhibitor, or combinations thereof.

The inventors have additionally found that the highly densified ceramic can be used alone for controlled release purposes, or it may be used in combination with a second part. By embedding the highly densified ceramic in a second part, it is possible to further modify and reduce the release. Accordingly, a pharmaceutical composition according to the invention may optionally further contain a second part comprising one or more pharmaceutically acceptable excipients, a therapeutically, prophylactically and/or diagnostically active substance (can be the same or different from that contained in the highly densified ceramic), one or more bioresorbable ceramics (can be the same or different from that contained in the highly densified ceramic, or may be mixtures of different ceramics), or one or more densified or highly densified ceramics e.g. containing different active substances and/or having different release characteristics compared with the first part. In the event that the second part comprises a bioresorbable ceramic it may be in non-hydrated, semi-hydrated, partly hydrated or fully hydrated form. The choice depends on the particular use. In some cases, it may be suitable to use a form that is hydratable, e.g. in order to further delay the release of the active substance, whereas it in other situations is suitable to use a hydrated form. Moreover, an active substance contained in a second part may be for substantially immediate release. The present invention thus provides a flexible delivery system, wherein parts of densified, highly densified and non-densified ceramics all or some of them containing one or more, the same or different, active substance, can be combined to obtain a desired release rate and release time.

In those cases, where a ready-to-use product is obtained by hydrating a second part comprising a bioresorbable and hydratable ceramic, it may be advantageous either to incorporate an organic acid comprising a carboxylic acid function in the composition or to add it to the water that is used to initiate the hydration. It is believed that such a compound delays the hydrating process and, thus, enables administration of the ready-to-use product over a specific period of time before it cures (i.e. the administration does not need to be immediately after the ready-to-use product is prepared).

Moreover, the second part may comprise a gelling agent, a swelling agent or a second bioresorbable and hydratable ceramic, which at least partly surrounds the highly densified ceramic. As used herein the term "at least partly surrounds" is used to describe e.g. a coating of layer of the second part covering the densified part, or a matrix in which the densified part is embedded, or a carrier, which is used to administer the densified part. The second part may also be a gel or a paste or a viscous medium.

Suitable gelling or swelling agent may be selected from the group consisting of: alginic acid, alginates, carboxymethylcellulose calcium, carboxymethylcellulose sodium (Ac-Di-Sol), crospovidone, hydroxypropylcellulose, hydroxypropylmethylcellulose (HPMC), low substituted hydroxypropylcellulose (L-HPC), microcrystalline cellulose, polacrilin potassium, polyacrylic acid, polycarbofil, polyethylene glycol, polyvinylacetate, polyvinylpyrrolidone, polyvinylpyrrolidone, plasdone, sodium croscarmellose, sodium starch glycolate (Explotab), and starches, and mixtures thereof.

When an optional second part of a pharmaceutical composition according to the invention comprises a second bioresorbable and hydratable ceramic it may further contain a second sorbed aqueous medium. Preferably said second sorbed aqueous medium is water. Said second bioresorbable and hydratable ceramic may be chosen from any suitable hydratable ceramic such as a non-hydrated, hydrated, semi-hydrated or partly hydrated ceramic selected from the group consisting of calcium sulphate such as, e.g., α-calcium sulphate, β-calcium sulphate; calcium sulphate hemi-hydrate; calcium phosphate; calcium carbonate; calcium fluoride; calcium silicate; magnesium sulphate; magnesium phosphate; magnesium carbonate; magnesium fluoride; magnesium silicate; barium sulphate; barium phosphate; barium carbonate; barium fluoride; and barium silicate; and mixtures thereof. In a preferred embodiment of the invention, the second bioresorbable and hydratable ceramic is non-hydrated, hydrated, semi-hydrated or partly hydrated calcium sulphate such as, e.g., α-calcium sulphate, β-calcium sulphate or calcium sulphate hemi-hydrate, or mixtures thereof. The second bioresorbable and hydratable ceramic according to the invention may be used as received in the pharmaceutical composition, or alternatively, be densified as described above for the highly densified ceramic.

A pharmaceutical composition according to the invention that contains a second part, may furthermore comprise one or more therapeutically, prophylactically and/or diagnostically active substances in said second part. These active substances may be the same or different from the one or more active substance incorporated in the highly densified ceramic.

In a pharmaceutical composition according to the invention, a highly densified ceramic may be fractured into smaller fragments/granules (typically 50-500 μm) and these granules/fragments may be incorporated into a second part. The hereby provided pharmaceutical composition can be used as an injectable paste, which solidifies in-vivo, or alternatively, may be moulded and solidify in vitro and positioned as pre-cured bodies in vivo. It is especially useful to embed the highly densified ceramic in a second ceramic such as calcium sulphate hemi-hydrate. It is hypothesized that the modified and/or reduced drug release rate achieved by embedding the highly densified ceramic containing the active drug(s), is explained by the additional precipitation of calcium-sulphate di-hydrates onto the surface and into fissures of the densified part. Accordingly, in one embodiment of the invention fragments of the highly densified ceramic are embedded in the second part. Such fragments of the highly densified ceramic may additionally be coated with a ceramic or polymeric layer.

However, another way of producing a controlled release pharmaceutical composition with both a highly densified part and a second part is the covering of pre-densified and hydrated bodies, e.g., grains, rods, pellets or any other geometry, with a second layer, e.g., a layer of a second bioresorbable and hydratable ceramic, said layer is allowed to hydrate while being in close contact with the pre-densified bodies. The hence achieved hydrated layer contributes to the sealing of the highly densified ceramic.

By combining a highly densified ceramic comprising an active substance, with a second part additionally containing the same or different active substance, it is furthermore possible to achieve a pharmaceutical composition characterized by a two-stage release pattern. The active substance contained in the second part may give a boost release, whereas the active substance incorporated in the highly densified ceramic, gives a prolonged controlled release.

The pharmaceutical composition according to the present invention may be employed in a semi-solid or solid form in several different embodiments, for e.g. parenteral use, that is for example:

a) as a highly densified ceramic in the form of e.g. tablets, beads, pins, rods, grains, needles etc., which are to be positioned at a suitable location in the living body;

b) as a highly densified ceramic in the form of e.g. tablets, beads, pins, rods, grains etc., covered with a layer or embedded in a second part, which provides further sealing by being hydrated in contact with the densified part;

c) as a highly densified ceramic shaped as e.g. grains or granules, which are positioned in the body e.g. by being injected together with a liquid carrier and hereby dispersed in the tissue;

d) as a highly densified ceramic shaped as e.g. grains or granules, which are mixed with a second part comprising a suitable gelling or swelling agent or a second bioresorbable and hydratable ceramic, optionally together with a second aqueous medium, to form a paste, which is positioned in the body either before or after hydration, i.e. it may either cure in vitro or in vivo.

The pharmaceutical composition according to the invention may further comprise other additives or other pharmaceutical excipients to modify the micro-structure and the release rate, e.g. hydrophobic modifiers such as stearic acid and Mg—(Na—) stearate, hydrogels, bioresorbable polymers or other polymeric compounds, which can further reduce the porosity and modify the release rate from the carrier.

Optionally, the pharmaceutical composition of the invention may also contain non-hydratable ceramics and metallic additives. The purpose of such additional component is increased radio-opacity, improved mechanical strength or solidification rate control. Established radio-opacity additives are barium salts or metals such as gold, zirconium or tantalum and their oxides. Furthermore, the hydration process and thereby the properties of the hydrated materials may be controlled by suitable additives. For example, properties such as the rheology of the non-solidified paste, the curing rate, and the mechanical properties of the solidified material can be steered to be most useful for the medical purpose(s) of the pharmaceutical composition.

Method of Preparing a Composition According to the Invention

Another aspect of the present invention relates to a method of preparing compositions according to the present invention, the essential feature of said method is the simultaneous densification and hydration, whereby the highly densified ceramic is obtained. The method comprising the steps of:

i) mixing one or more bioresorable and hydratable ceramics with one or more therapeutically, prophylactically and/or diagnostically active substances; and ii) densifying the mixture obtained in i) by applying an external pressure, and iii) hydrating the ceramic during the densification in step ii) by adding water to the resulting mixture from step i) in an amount corresponding to from about 20% to about 110% of the stoichiometric amount necessary to fully hydrate the one or more ceramics, whereby a highly densified and at least partly hydrated ceramic is obtained with a porosity of at the most 10%.

The hydration or partly hydration of the hydratable ceramics takes place during the densification, by adding water before or during step ii). As described previously the inventors have found that the addition of water (e.g. in the form of an aqueous medium) can be done in a one or two step procedure to obtain a one or two step hydration improves the densification further. The one step procedure involves addition of the aqueous medium before the densification, whereas the two step procedure typically involves addition of a part of the aqueous medium before or during the densification, and another part added after the pressurizing step, then the densification may be further improved. Accordingly, an optimized densification effect is achieved by pressurising a preformed body of e.g. calcium sulphate with a less than stoichiometric amount of aqueous medium (e.g. less water than what is bonded in an ideal full hydration). The remaining aqueous medium is favourably added in a post-hydration step after removal of the pressure.

To achieve a high degree of compacted materials the pressure in step ii) is held for at least about 10 minutes such as, e.g., at least about 15 minutes, at least about 20 minutes, at least about 30 minutes or at least about 45 minutes, in order to achieve hydration or partly hydration under densification.

Optionally, organic acids comprising a carboxylic acid group, such as acetic acid, citric acid, succinic acid and tartaric acid and the like, can be added to the hydratable ceramics prior to the densification in step ii) to delay the chemical reaction between the hydratable ceramics and the aqueous medium, i.e. the curing of the ceramic is delayed.

Several techniques may be used to apply the external pressure, for example uniaxial pressing or isostatic pressing (hot or cold). Cold Isostatic Pressing (CIP), applied to preformed bodies of calcium sulphate containing the selected active components, has been found to be an effective method to produce highly densified and homogenous bodies. For an optimal densification, the ceramic bodies may be covered with e.g. a capsule (e.g. an elastic balloon) during pressurising. The applied pressure should be at least 100 MPa such as, e.g., at least about 200 MPa, preferably 300 MPa or above. However, the pressure required is dependent on the pressing apparatus employed. Thus, the above-mentioned pressures are suitable for use in case of CIP, whereas in the case of e.g. a uniform uniaxial pressing, pressures are normally applied that are higher such as, e.g., at the most about 200 MPa, preferably about 300 MPa or more, about 400 MPa or more, or about 500 MPa or more.

Optionally, disintegration (crushing) the hydrated ceramic to obtain a particulate material that is suitable for use in manufacturing of pharmaceutical compositions (e.g. also dual or multiple compositions) can e.g. be used to make an injectable paste, which solidifies in-vivo, or alternatively, may be moulded and solidify in vitro and positioned as pre-cured bodies in vivo. The disintegrated hydrated material may also be mixed with one or more pharmaceutically acceptable excipients.

In one embodiment of the method according to the invention, the hydration is performed as a post-hydration step iii). In a preferred embodiment, the hydration is performed as an admixture of an aqueous medium in step i), and in a more preferred embodiment the hydration is performed as both an admixture of aqueous medium in step i) together with an post-hydration step iii).

In the method according to the invention, the applied external pressure in step ii) may be of at least 50 MPa such as, e.g., at least 100 MPa, at least 200 MPa or at least 300 MPa.

Depending on the particle size of the commercial purchased bioresorbable and hydratable ceramic, the method may furthermore, as describe above, comprise a step of milling the one or more bioresorbable and hydratable ceramics prior to step i), or optionally a step of milling and granulating the one or more bioresorbable and hydratable ceramics prior to step i), as to enhance the densification further. The milling may be performed by dispersing the ceramic in an organic solvent, e.g. an alcohol like ethanol or iso-propanol. In such a case, the active substance may be dissolved in the same solvent and added during or after the milling process in order to ensure a suitable homogeneous distribution of the active substance in the ceramic. In some embodiments, the active substance may be encapsulated in the ceramic, e.g. by mixing the active substance with part of the ceramic, subjecting this mixture to partly hydration and then adding the remaining part of the ceramic. In a preferred embodiment of the invention, the mean particle size of the one or more bioresorable and hydratable ceramics employed in step i) is at the most about 10 µM. The porosity of the highly densified ceramic obtained in step ii) is preferably at the most about 5%.

As described above, a highly densified ceramic can be used alone for controlled release purposes, or it may be used in combination with a second part. Therefore, in another embodiment of the invention, the highly densified ceramic is embedded in a second part, and the method according to the invention accordingly further comprises iv) mixing the highly densified ceramic with a second part, as defined above.

A third aspect of the present invention relates to a method of treating diseases comprising administering a pharmaceutical composition according to the invention to a patient. In a preferred embodiment of said method, the disease is cancer, and in a more preferred embodiment, the disease is a prostate related disease such as benign prostate hyperplasia, prostate cancer or prostatite. The pharmaceutical composition may be administered parenterally or by implantation.

Moreover, the present invention provides kits as defined in the appended claims for the preparation of a composition according to the invention.

All details and particulars mentioned under the main aspects of the invention apply also for all other aspects of the invention.

FIGURE LEGENDS

FIG. 1
Microstructures of (a) non-compacted and (b) compacted hydrated calcium sulphate.

Figure 2:
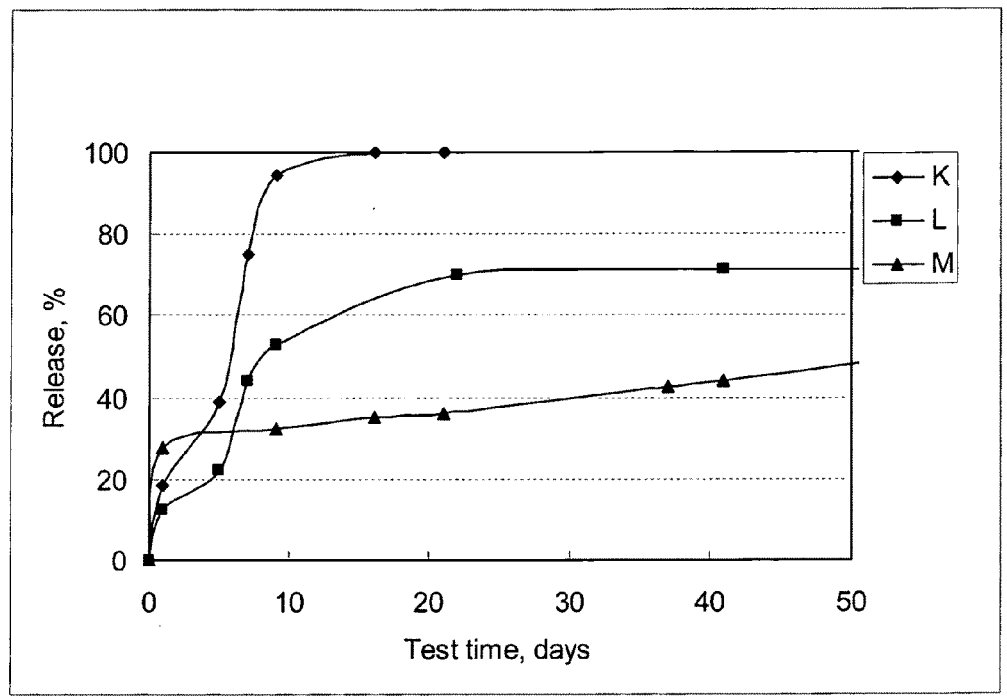

FIG. 2
In vitro release rate vs time for three types of calcium sulphate/2-hydroxyflutamide compositions, K, L and M.

Figure 3:
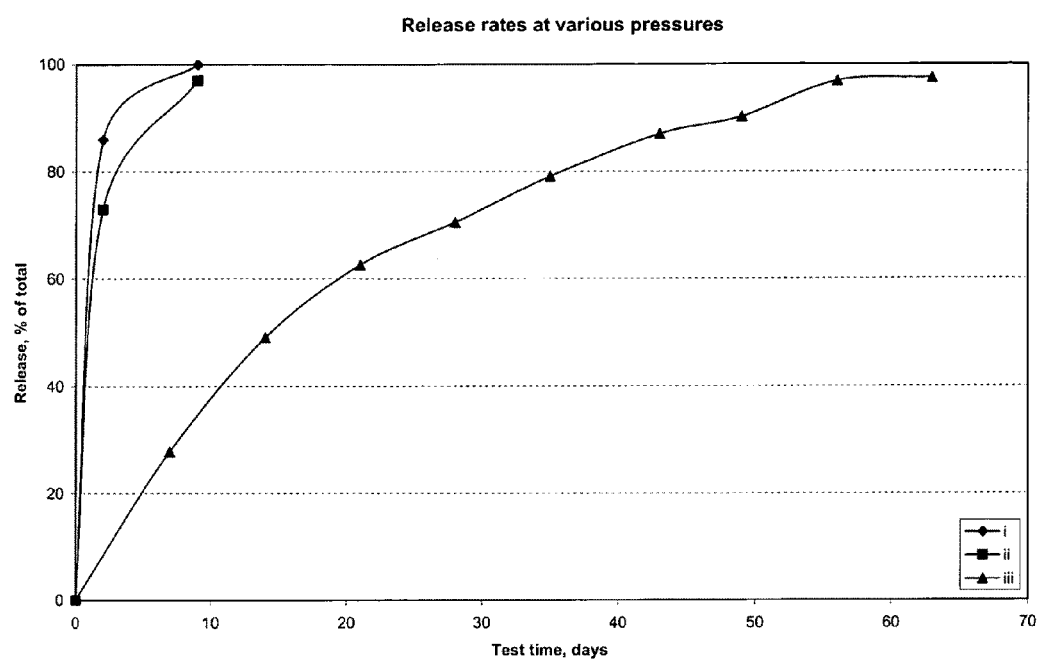

FIG. 3
In vitro release rate vs time of differently compacted calcium sulphate/2-hydroxyflutamide compositions (i) (ii) and (iii).

Figure 4:
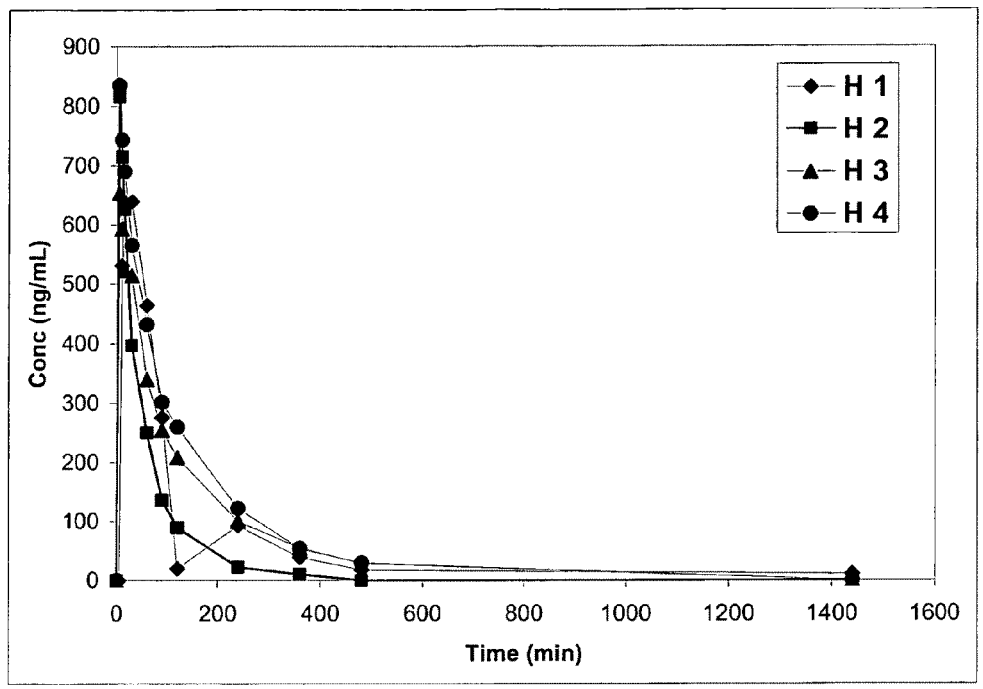

FIG. 4
The individual plasma concentration vs time profiles of 2-hydroxyflutamide after a single intravenous bolus administration of 25 mg 2-hydroxyflutamide to four dogs (H1, H2, H3 and H4).

Figure 5:
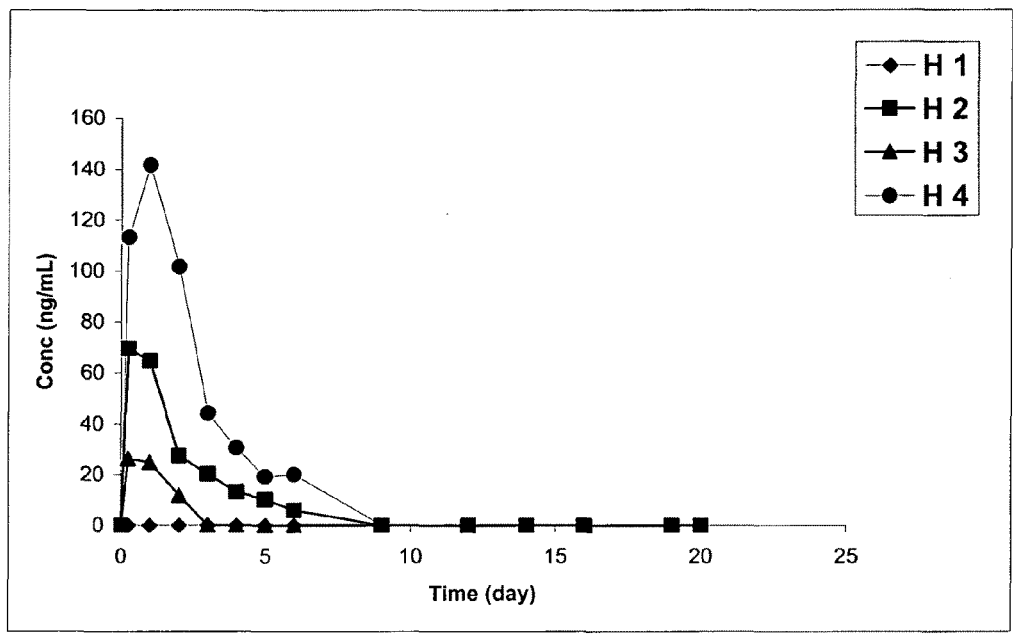

FIG. 5
The individual plasma concentration vs time profiles of 2-hydroxyflutamide (F—OH) after a single administration of controlled release implants with different doses of 2-hydroxyflutamide in the prostate of four dogs (H1—control, H2—60 mg F—OH, H3—30 mg F—OH and H4—120 mg F—OH).

Figure 6:
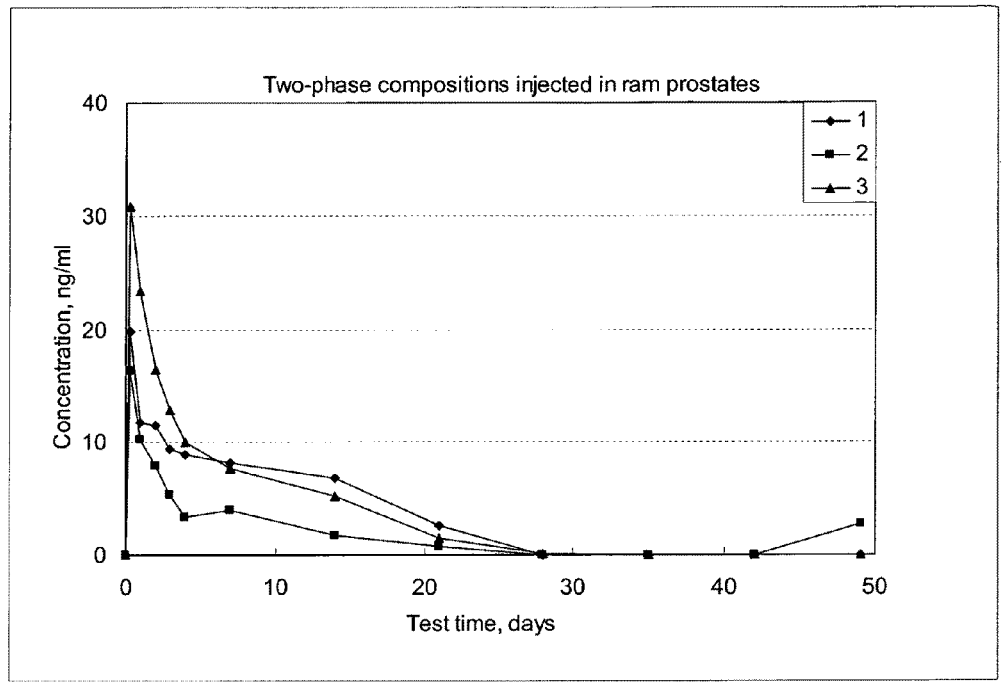

FIG. 6
Selected examples of the individual plasma concentration vs time profiles of 2-hydroxy-flutamide after a single administration of controlled release implants in the prostate of rams treated with 500 mg (3) and 250 mg (1 and 2) of 2-hydroxyflutamide, respectively.

Figure 7:
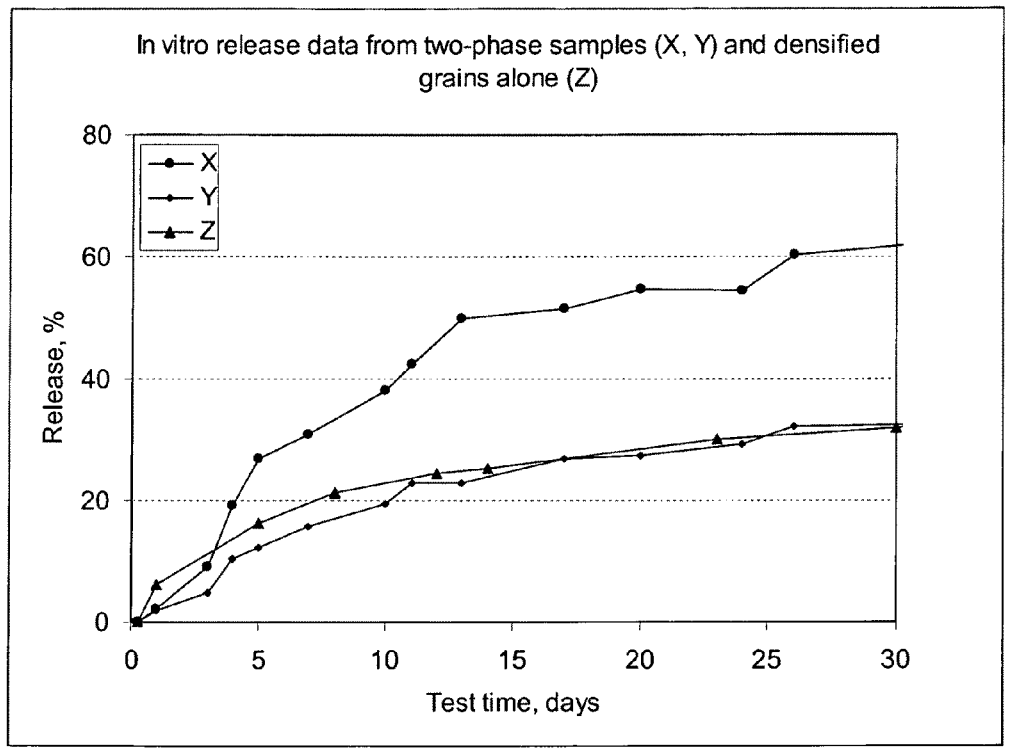

FIG. 7
The in vitro cumulative release vs time for three types of calcium sulphate/2-hydroxyflutamide compositions/microstructures: X, Y and Z.

The following examples are intended to illustrate the invention without limiting it thereto.

EXAMPLES

Example 1

This example illustrates the effect of pressure on the porosity of calcium sulphate bodies. Three samples (labelled A, B and C) were manufactured from calcium-sulphate hemi-hydrate powder from Sigma-Aldrich (Cat. no. 30, 766-1) and deionised water:

A: 1.0 g of as received (unprocessed) calcium-sulphate hemi-hydrate powder was mixed with 2.0 g of water to a paste. The paste was used to form 12 mm in diameter and 3 mm high cylinders using a mould and was left to cure. A scanning electron microscopy image of a fracture surface of a sample of type A is provided in FIG. 1a.

B: One g of as-received calcium-sulphate hemi-hydrate powder was axially pressed in dry state at 100 MPa in a 12 mm in diameter cylindrical die. The compressed tablets were soaked in water and left to cure.

C, 1.0 g of as-received calcium sulphate powder was axially pressed in dry state at 200 MPa in a 12 mm in diameter cylindrical die. The compressed tablets were soaked in water and left to cure.

The following porosities were measured by weighing the tablets and comparing to the tabulated theoretical full density value of fully compacted calcium-sulphate-di-hydrate, 2.32 g/ml.

TABLE 1

Porosity values.

| Sample | Porosity, vol. % |
| --- | --- |
| A | 50 ± 10 vol. % |
| B | 25 ± 4 vol. % |
| C | 21 ± 1 vol. % |

Example 2

This example illustrates the effect of hydration technique on the porosity of a hydrated and compressed calcium sulphate. The example shows that partial hydration under an applied pressure increases the obtainable density of the pharmaceutical material. In this example the used powder was milled prior to compression. The calcium-sulphate hemi-hydrate powder from Sigma-Aldrich (Cat. no. 30, 766-1) was milled 1 hr in a ball mill. Samples D-F are made from this powder.

The milling procedure was as follows: 100 g of the calcium sulphate powder was mixed with 55.8 g of iso-propanol and 500 g of 16 mm diameter alumina milling balls were rotated at 100 rpm in a 500 ml polyethylene cylindrical container. The milling needs to be performed in a non-aqueous medium such as an alcohol.

The particle size was analysed with a Sedigraf. The results are provided in Table 2. For the as-received powder, 50% of the grains are less than 10.5 μm in diameter, i.e. $d_{50}=10.5$ μm. After 1 hr of milling the grain size is characterised by $d_{50}=5.5$ μm; and after 2 hrs of milling the powder is characterised by $d_{50}=2.7$ μm. See table 2.

TABLE 2

Grain size as a function of milling time.

| Milling conditions | Powder grain size, $d_{50}$ |
|---|---|
| As-received | 10.5 μm |
| 1 hr of milling | 5.5 μm |
| 2 hrs of milling | 2.7 μm |

Three types of samples were produced (labelled D, E, F):

D: 1.0 gram of calcium-sulphate hemi-hydrate powder was compressed uniaxially in a cylinder shaped mould of 12 mm diameter with an axial pressure of 200 MPa. To the tablets 0.19 g of de-ionised water was added after compression. The water was absorbed by the dry ceramic. 0.186 g of water is the optimum stoichiometric amount absorbable in the hydration process for 1.0 g of calcium sulphate hemi-hydrate as it completely forms the di-hydrate, according to:

$$CaSO_4 \cdot 0.5H_2O(s) + H_2O(l) \rightarrow Ca^{2+} + SO_4^{2-}(\text{solution}) \rightarrow CaSO_4 \cdot 2H_2O(s)$$

E: Tablets were produced from the same amounts of calcium-sulphate hemi-hydrate powder and de-ionized water in the same pressing equipment at 200 MPa as for sample D, but now by first adding the water to the powder and mixing together, and thereafter compressing the wetted powder to tablets. No water was added afterwards. The tablets were curing during the application of the external pressure. A scanning electron microscopy image of a fracture surface of a sample of type E is provided in FIG. 1b.

F: Tablets of the same amounts of calcium-sulphate hemi-hydrate and de-ionized water were produced by first adding half of the total amount of water (0.093) to the powder and mixing, and thereafter compressing to tablets uniaxially. After the compaction process, the second half of water was added to the tablet in a post-hydration step.

The following porosities were measured by weighing the tablets and comparing to the tabulated theoretical full-density value of fully compacted calcium sulphate-di-hydrate, 2.32 g/ml:

TABLE 3

Porosity values.

| Sample | Porosity, vol. % |
|---|---|
| D | 20-22 vol. % |
| E | 10-15 vol. % |
| F | 5-7 vol. % |

This example illustrates that hydration under an applied pressure produces a higher final density of the material compared to hydration of a pre-compacted material. However, adding all the water prior to compression is not optimal. Instead, having part of the hydration take place under pressure, and adding more water post-pressure is more efficient in producing a dense material.

It is hypothesised that this effect is explained by that only a limited amount of water can stay in the compacted sample as it is compressed by the applied pressure, and hence is available for the hydration reaction. A surplus of water creates residual porosity as the hydration proceeds under the applied pressure.

Example 3

This example illustrates porosities achievable with powder milled for two hours by using cold isostatic pressing as an alternative to uniaxial pressing, and by holding the pressure during the hydration to achieve high degree of compacted materials. The example also illustrates the use of freeze granulation to produce a dry and granulated powder, and the addition of a fatty organic additive (stearic acid) to the composition. Four sample types were prepared for this example, labelled G, H, I, J:

G: These samples were produced with isostatic pressing using a Loomis press at 200 MPa. Each sample tablet was made from 1.0 gram of as-received calcium-sulphate hemi-hydrate powder from Sigma-Aldrich (Cat. no. 30, 766-1). First, uniaxial pressing (about 20 MPa) was used to form a loosely pressed tablet of 12 mm diameter and about 2 mm in thickness. The hence prepared samples were wetted with 0.186 g of deionised water and placed individually in sealed balloons. Immediately after application of the water, the samples were positioned in the press and exposed to an isostatic pressure of 200 MPa at room temperature (20° C.). The pressure was held for 30 minutes. The samples were thus hydrated under isostatic pressure. The isostatic pressure reduces both the diameter and thickness of the samples significantly.

H: These samples were produced with a similar procedure as the samples G, using isostatic pressing, but from powder milled for 1 hr, with the milling technique described in example 2, and with only half of the water (0.93 g) added during the isostatic pressing cycle. The remaining water was exactly added to the tablets after pressurising by dropping over the tablets positioned on a balance.

I: These samples were produced as the samples G and H, again using isostatic pressing, but from a powder milled for 2 hrs, as described in example 2, and with only half of the water (0.93 g) added during isostatic pressurising. Further the powder was granulated prior to pressurising with a freeze granulation technique. The remaining water was added to the tablets by dropping over the tablet positioned on a balance, after the isostatic pressing.

The freeze granulation process was performed as follows: A suspension of the powder mix and iso-propanol is sprayed with an air jet into a container with liquid nitrogen. The powder suspension drops are momentarily frozen as they enter the nitrogen, forming granules of a homogenous composition. In a subsequent freeze drying step the ice is removed by sublimation in a vacuum chamber without any segregation of the microstructure of the granules. The result is spherical granules with the composition of the starting powder mix.

J: These samples were produced as the samples I, but with an additive of 0.5 or 1.0% stearic acid to the starting powder.

The following porosities were measured comparing to tabulated theoretical full density calcium sulphate-di-hydrate:

TABLE 4

Porosity values.

| Sample | Porosity, vol. % |
| --- | --- |
| G | 16-17 vol. % |
| H | 6.0-7.0 vol. % |
| I | 4.5-5.0 vol. % |
| J | 4.0-5.0 vol. % |

This example illustrated the positive effect of a reduced grain size of the powder, here achieved by milling, on the achievable low porosity of the densified material. However, from comparing example 2 and 3, there was no measurable difference between 1 hr and 2 hrs milling, although the difference between no milling and 1 hr was significant (as measured with a sedigraph).

The example also illustrates the possibility of using a freeze granulation technique. This has the advantage of producing powders of better flowability compared to non-granulated powder. Its effect on material density was however low. The example further shows that a fatty additive as stearic acid can be incorporated in the composition. Its effect on porosity was however low in these tests. The additive however makes the test samples more water repellent.

Example 4

This example serves to verify the porosity values of the preceding examples by performing additional measurements on a selection of samples with a more precise pores size measurement method.

The pore-structure of a selection of samples was measured with a Hg porosity measurement method (Micromeritics AutoPore III 9410). The method quantifies the overall porosity and the dimensions of the pores.

With the mercury method, the porosities of sample F from example 2 was 4.8%, sample H from example 3 was 4.0% and sample I from example 3 was 2.8%, see Table 5.

This confirms the order of magnitude of the porosity values as measured from the dimensions of the samples and the theoretical full density.

TABLE 5

Porosity values form the Hg-method.

| Sample | Porosity (Hg) vol. % | Porosity weight vol. % |
| --- | --- | --- |
| F | 4.8 | 5.0-7.0 |
| H | 4.0 | 6.0-7.0 |
| I | 2.8 | 4.5-5.0 |

Example 5

This example illustrates how the addition of 2-hydroxyflutamide, the pharmacological active metabolite of flutamide, to a densified calcium sulphate material can be achieved. 2-hydroxyflutamide is of particular interest to this patent. The example also provides typical drug release rate data for such compositions obtained in an in vitro model.

Sample Preparation

Three different types of samples with 2-hydroxyflutamide in a matrix/carrier of calcium sulphate was prepared and evaluated regarding in vitro/in vivo drug release and in vivo pharmacokinetics, labelled K, L and M:

K: These samples are non-compressed fully hydrated calcium sulphate samples with 2-hydroxyflutamide. For each sample, 4.5 mg of crystallised 2-hydroxyflutamide in a fine grained powder form was added to 0.5 g of calcium-sulphate hemi-hydrate as-received powder and mixed. 1.0 g of sterile water was added (ratio 2:1 by weight) to form a paste and tablets 12 mm in diameter were moulded and left to cure.

L: These samples are isostatically compressed tablets with the same amount of 2-hydroxyflutamide per sample as the K samples in this example.

To produce the samples, the as-received powder was milled for 2 hrs with the method described in Example 3.

2-hydroxyflutamide was dissolved in isopropanol (Ph Eur from Merck, CAS 6-63-0). The milled calcium-sulphate hemi-hydrate powder was added to the solution. An ultrasonic bath (Elma Trans-sonic T700) was used to de-agglomerate the powder.

The dispersion was dried with an evaporator of type Buchi Rotavapor R110 to forming a calcium sulphate hemi-hydrate powder with precipitated 2-hydroxyflutamide. Proportions were 4.5 mg of 2-hydroxyflutamide to 0.5 g of calcium sulphate powder. (Also freeze granulation was evaluated successfully to produce the calcium sulphate hemi-hydrate 2-hydroxyflutamide mix).

Uniaxial pressing at about 20 MPa was used to form a loosely pressed tablet of 0.5 g of calcium-sulphate hemi-hydrate at low pressure, about 12 mm diameter and 2 mm thick. For densification the samples, they were each wetted with 0.046 g of sterile water and placed individually in balloons. The samples were exposed to an isostatic pressure of 200 MPa immediately after wetting, in an oil-based pressure equipment (Loomis isostatic press). The pressure was held for 30 minutes. The samples were thus hydrated under isostatic pressure. The isostatic pressure reduces both the diameter and thickness of the samples considerably. A further 0.046 g of sterile water was added afterwards to reach full hydration.

M: Samples of the L type were crushed (with a Fritsch Pulverisette type 1) and sieved (with mesh sieves from Retsch) to crushed grains of size 100-500 μm.

To create a paste of calcium sulphate containing the densified grains, the grains were mixed with non-hydrated and as-received calcium-sulphate hemi-hydrate powder in proportions 1:2 by weight. Paste of this powder was used to mould samples, creating a two-phase composition with hydrated and compacted grains containing 2-hydroxyflutamide in a matrix of non-compacted and hydrated calcium sulphate. Test samples containing 4.5 mg of 2-hydroxyflutamide (i.e. 0.5 g of compressed grains) were prepared for in vitro release tests.

In Vitro Drug Release Tests

The prepared 0.5 g tablets with 4.5 mg of 2-hydroxyflutamide, and the moulded samples with crushed grains in a non compacted matrix, were placed in glass containers containing 60 ml of sterile NaCl saline solution (9 mg/ml) incubated in a water bath at 37° C.

At each sample collection occasion 4 ml of the saline were collected, and replaced with 4 ml of fresh sterile saline. Before a sample was withdrawn the in vitro release vessel was gently shaken.

The samples were stored in plastic capsules and frozen directly after collection and stored at −20° C. until analysis. The liquid samples were analysed with respect to their concentration of 2-hydroxyflutamide using LC-MS-MS chromatography.

In Vitro Drug Release Results

The in vitro drug release rate data are recalculated and presented as percent released and dissolved of 2-hydroxyflutamide in relation to the total amount of 2-hydroxyflutamide in the formulation over time. The data are shown in FIG. 2.

The non-compacted formulation releases more than 90% of the 2-hydroxyflutamide in about 10 days (sample K).

The compacted tablets (L) releases 2-hydroxyflutamide at a similarly high rate for the first 10-15 days, thereafter the release rate was reduced. After 40 days about 70% of the total amount of 2-hydroxyflutamide is released from the formulation (sample L).

The M sample of densified granules in a non-densified matrix provides a very fast release during the first day, but thereafter the release rate is lower than for the other samples. After 40 days the release has reached about 40%, clearly lower than for the L formulation.

Example 6

This example illustrates the effect of the applied external pressure on the release rates of 2-hydroxyflutamide from differently compacted calcium sulphate bodies. This example also illustrates how the addition of 2-hydroxyflutamide, the pharmacological active metabolite of flutamide, to a densified calcium sulphate material can be achieved. 2-hydroxyflutamide is of particular interest. The example provides typical drug release rate data for such compositions obtained in an in vitro model.

Three different samples (labelled i, ii and ii) were manufactured from calcium-sulphate hemi-hydrate powder from Sigma-Aldrich (Cat. no. 30, 766-1), sterile water and 2-hydroxyflutamide. The manufacturing procedure was as follows:

The calcium-sulphate hemi-hydrate powder from Sigma-Aldrich (Cat. no. 30, 766-1) was milled for grain size reduction (by tumbling in a 1.0 liter plastic container) for 48 hrs in iso-propanol (Ph Eur from Merck, CAS 6-63-0) with ceramic milling balls to a grain size corresponding to 50% below 3 microns and 80% below 6 microns. The original powder had a grain size of 50% below 10 microns.

10 g of 2-hydroxyflutamide was completely dissolved in 75 g of iso-propanol. The dissolution was accelerated with an ultrasonic bath (Elma Trans-sonic T700). 100 g of milled calcium sulphate hemi-hydrate was added to the 2-hydroxyflutamide-isopropanol solution, and stirred until forming a homogenous slurry. An ultrasonic bath was used to de-agglomerate the powder. The dispersion was dried with an evaporator (of type Buchi Rotavapor R110) to form a calcium sulphate hemi-hydrate powder with precipitated 2-hydroxyflutamide. The dried powder mix was passed through a 355 micron sieve to achieve a de-agglomerated and easily flowing powder.

Alternative methods were evaluated to form the calcium sulphate hemi-hydrate 2-hydroxyflutamide mix. As one alternative, freeze granulation was evaluated successfully to produce the calcium sulphate hemi-hydrate 2-hydroxyflutamide mix. As a second alternative dry mixing was evaluated successfully. The crystallized 2-hydroxyflutamide was passed dry through a 20 micron sieve to form a fine grains powder which could be directly mixed with the calcium sulphate hemi-hydrate. However, the evaporation of a (non-aqueous) solvent suitable for 2-hydroxyflutamide (such as iso-propanol) seems to be a practical manufacturing process.

The hence achieved powder mix was used to produce three types of samples by uniaxial compression. Rods of weight 10 g were pressed in a stainless steel pressing tool with cavity dimensions of 8×60 mm. The height of the rods became about 8-10 mm depending on the applied pressure. The rods were densified with loads of 0.75 kN and 10 kN; corresponding to 1.5 MPa and 20 MPa.

Rods compressed at 1.5 and 20 MPa (samples (i) and (ii), respectively) were wetted with 1.5 g of water and left to hydrate under a Petri-disk lid over night. The water was added with a pipette, 0.375 mg on each long-side of the rod. From the hydrated rods pieces of 0.1 g were cut. These pieces were used for in vitro release tests, as further described below.

To manufacture sample (iii) a second compression step was explored. A rod pre-compressed at 20 MPa was treated at a higher pressure in a second step after being wetted. The rod was wetted with a total of 1.5 g of water in the same way as above, but immediately after wetting the rod was encapsulated in a balloon and exposed to an external isostatic pressure of 300 MPa for 30 minutes, using a oil-based cold-isostatic press from Jemtab AB. All compressions were performed at room temperature.

The highly densified material formed by the external isostatic pressure, was tested in a granular form. To produce grains or granules the densified rod, it was crushed using a ultra-centrifugal mill from Retsch. After crushing grains of size 125-500 µm were selected by sieving. The sieved grains were mixed with the original non-milled calcium sulphate hemi-hydrate powder, from Sigma-Aldrich (Cat. no. 30, 766-1), in proportions 1:2 by weight, thereby forming a hydratable powder mix.

From this powder mix, samples for in vitro release tests were moulded and cured. To mould samples, 4.0 g of the powder was mixed with 2.5 g of a solution containing 1.0 wt. % of acetic acid and 1.0 wt. % of methylcellulose to form a smooth paste. A syringe was used to form 1.0 g test lumps of the paste. The moulded lumps of paste were left to hydrate over-night, forming solid pieces used for release tests.

The granular form of the densified and simultaneously hydrated ceramic carrier with active agent, used as paste with a water based diluent, is of particular interest, and has been evaluated also after sterilisation. The powder mix was sterilised by gamma-radiation, and the aqueous diluents by heat in an autoclave.

The samples (i), (ii), and (iii) were evaluated regarding release rates in an in vitro model. The release tests were performed by placing the test pieces in glass containers containing 100 ml of sterile NaCl saline solution (9 mg/ml) incubated at 37° C. Samples of the saline solution were taken at predetermined intervals and analysed with respect to their concentration of 2-hydroxyflutamide using LC-MS-MS chromatography. At each sample collection occasion 20 ml of the saline was collected, and replaced with 20 ml of fresh sterile saline. Before a sample was withdrawn the in vitro release vessel was gently shaken. The samples were stored in plastic capsules and frozen directly after collection and stored at −20° C. until analysis.

The release results are presented in FIG. 3. Both the samples (i) and (ii), manufactured with one compression step at 1.5 and 20 MPa, release most of the encapsulated 2-hydroxyflutmaide after some 10 days in the in vitro model. The test samples based on the material densified and hydrated at 300 MPa release 2-hydrioxyflutamide over some 60 days.

The example illustrates the effect of hydration under an applied external compression on the release rate of active agents from a ceramic, hydratable, and resorbable matrix. The example also illustrates an interesting productification alternative of the densified and hydrated ceramic composition, as an injectable paste with densified granules.

Example 7

Manufacturing Process Description

A Highly Densified Ceramic According to the Invention

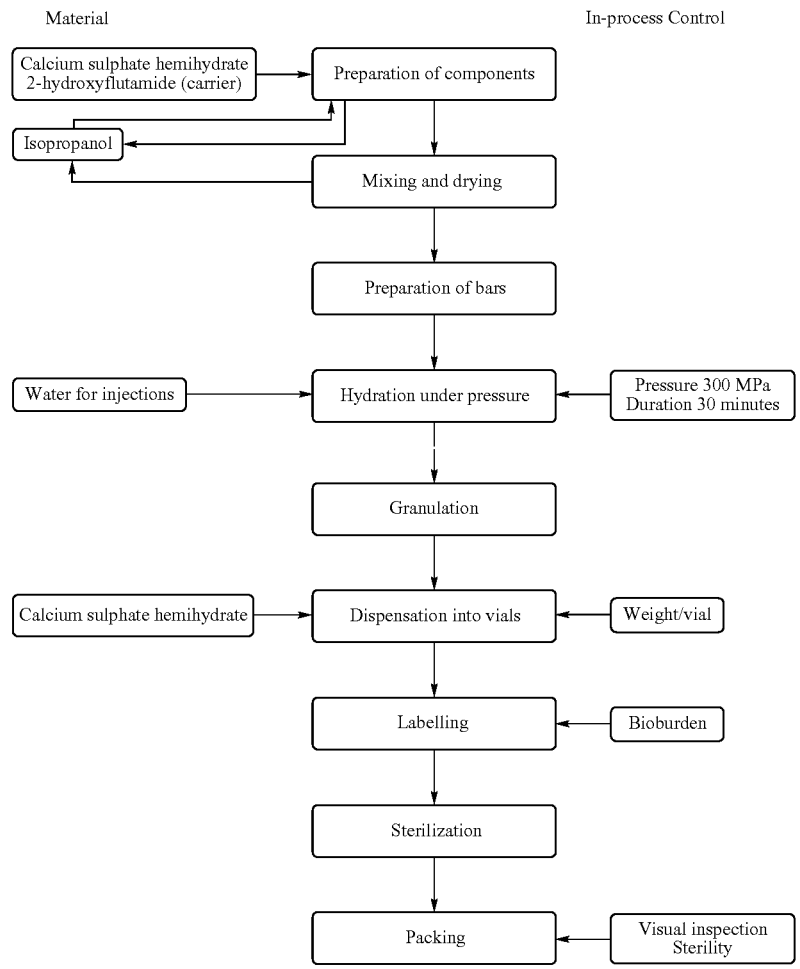

Control of Materials

Iso-propanol (assay >99.8%, water content <0.1%) and Water for injections, used in the manufacturing process, comply with the respective Ph Eur monographs.

Preparation of Components

The 2-hydroxyflutamine powder is weighed and dissolved in iso-propanol.

The calcium sulphate hemi-hydrate powder is weighed, mixed with iso-propanol and milled in a powder mill to fine particles. The iso-propanol is evaporated and the dried powder passed through a sieve.

Mixing and Drying

The finely milled and dried calcium sulphate hemi-hydrate powder is added to the 2-hydroxyflutamide solution in the ratio 1.0 g of calcium sulphate powder to 0.1 g of 2-hydroxyflutamide dissolved in iso-propanol.

The powder is de-agglomerated in the ultrasonic bath. The mixture is dried in an evaporator, and the dried powder is passed through a sieve.

Preparation of Bars

Bars of approximately 10 g, measuring approximately 60×8×10 mm, are prepared from the dried mixture by dry pressing.

Hydration Under Pressure

Approximately 1.5 g of Water for injections is added drop wise to each bar, and allowed to soak into the porous bar. Within one minute from the water addition the wetted bar is wrapped in aluminium foil and encapsulated in a balloon, immersed in the oil bath of the press and subjected to a pressure of 300 MPa. The pressure of 300 MPa is maintained for 30 minutes.

The balloon is removed and the bars are left to dry.

Granulation

The hard bars are crushed to fine granules and passed through two sieves with mesh sizes corresponding to the upper and lower limits of the desired granule size range. Material passing through the smaller mesh size (125 microns) is discarded. The discarded material constitutes approximately 50% of the total amount. Approximately two bars are prepared, hydrated and pressed at a time, and the procedure repeated until all material has been pressed and granulated.

Dispensation into Vials

The granules are manually dispensated into vials, using a balance equipped with a printer, 1.33 g per vial. A further amount of 2.66 g of as-received calcium sulphate hemi-hydrate is added to each vial (proportions 1:2 in weight).

The vials are stoppered and capped. The granules are mixed with the calcium sulphate hemi-hydrate by shaking the vial.

Labelling

The vials are labelled. Three vials are withdrawn for test of bioburden.

Sterilisation

Liproca Powder is sterilised by gamma radiation.

Packing

Samples are withdrawn for test of sterility, and the vials are visually inspected, prior to packing in boxes together with Liproca Diluent MC (i.e. water comprising methylcellulose) and Liproca Diluent HAc (i.e. water containing acetic acid).

Example 8

This example illustrates the reduced drug release rate achieved by densification of calcium sulphate as evaluated in animal models (in vivo). Two different animal models (male Labrador and male sheep) were applied in the evaluation of the in vivo drug release characteristics of calcium sulphate based controlled release implants containing 2-hydroxyflutamide.

Intravenous Bolus Dosing

First, an animal study was performed with 4 sexually mature Labrador dogs, aged 1 year, under approval by the Animal Ethics Committee of University of Gothenburg.

The male dogs (Labrador) were first given an intravenous single bolus dose of 2-hydroxyflutamide or 25 mg (10 ml solution) per animal during 30 seconds. The composition of the intravenous solution was sterile saline 54%, sterile polyethyleneglycol 400, 46% and 6% ethanol (95%).

After injection into vena jugularis, blood samples were taken at predetermined time points during 10 hours.

2-hydroxy-flutamide was rapidly eliminated after intravenous bolus administration and the elimination half-life was 1.75±0.2 hrs. The plasma-concentration time-profile of 2-hydroxy-flutamide for each dog is given in FIG. 4. After about 10 hrs the plasma concentration of 2-hydroxyflutamide was below the detection limit.

Non-Compacted Calcium Sulphate as Drug Carrier in Dog

One week later, the same animals as were given the intravenous dose of 2-hydroxyflutamide, were given a mixture of 2-hydroxy-flutamide and a non-compacted calcium-sulphate hemi-hydrate in the prostate tissue as a controlled release implant. The 2-hydroxy-flutamide doses were 0 (control), 30, 60 and 120 mg, and was given together with calcium sulphate as a single implant injection through the rectal route. The control animal was given the calcium sulphate implant without 2-hydroxy-flutamide.

To prepare the implant a calcium sulphate hemi-hydrate powder was mixed with sterile water and the active agent to form a paste. The sterilised calcium-sulphate hemi-hydrate power to water ratio was 1:2 and the dose of active agent was mixed with in total 0.8 ml of paste. The paste was injected into the prostate and solidified in vivo. The present implant composition has an in vitro release profile that is equal to the release profile K in FIG. 2.

The implant drug delivery system was inserted into the prostate tissue through the rectum by applying needles and ultrasound guidance. The animals were under general anaesthesia during the insertion procedure. The needle (15 cm long with an outer diameter of 0.9 mm) was inserted into the prepared rectum through the rectal and abdominal wall and positioned in the prostate tissue by ultrasound guidance. The implant dose was positioned into the prostate tissue as two thin strings of approximately 12 mm length and a diameter of 1-2 mm. Each animal were given an antibiotics for one week.

Blood samples were taken every day for the first week and then every second day for the two reaming weeks. The plasma concentration of 2-hydroxyflutamide was quantified with a HPLC-MS-MS method.

The preparation of the formulation was done under supervision of responsible pharmacist. The insertion and dosing of the sterile ceramic based implant into prostate tissue was performed by a responsible urologist.

Results—Non-Compacted Calcium Sulphate

The individual plasma concentration time profiles of 2-hydroxyflutamide are illustrated in FIG. 5 for the non-compacted samples. For the compositions used, the plasma concentrations of 2-hydroxyflutamide was below the detection limit (LOQ) nine days after the administration of the controlled release implant into the prostate gland. This was interpreted as that the release of the drug was at least almost complete nine days after administration into the prostate gland. This means that the in vitro drug release profile predict the in vivo drug release profile with rather high accuracy. It also demonstrate that the in vitro release method developed for this implant method is useful in the development of these implant formulations.

It was further concluded that:

The sustained release implant was successfully implanted in the prostate tissue with established surgical techniques, i.e. needles and ultrasonic guidance.

For the two higher single implant doses (60 and 120 mg) the tissue weight was reduced in comparison with the animals that were given the placebo and low single implant dose (30 mg). The prostate tissue was also softer than the control animal as well the animal receiving the low dose of implant.

It was also shown that the calcium sulphate prolonged the release of the active drug, and that the plasma concentration was low and no acute systemic mediated side-effects such as diarrhea was monitored after the implant dose. The in vivo release rate of 2-hydroxyflutamide was prolonged by 40-45 times as judged by the prolonged plasma half-life of 2-hydroxyflutamide in comparison with the corresponding pharmacokinetic variable after intravenous bolus dosing.

The histopathology showed that the implant was well tolerated and that the procedure did not cause any infections. The ceramic implant caused minimal inflammatory reactions in the prostate tissue.

Compacted Calcium Sulphate as a Controlled Release Implant in Male Sheep

Second, an in vivo animal study was performed with compacted calcium sulphate on 15 male sheep (ram) age between 1 year and 6 years. The study was approved by the Regional Animal Ethics Committee of Uppsala, Sweden.

The 15 male sexually mature sheep were divided into three separate groups. Two groups were given 2-hydroxyflutamide with a local implant delivery system in the prostate tissue. Each animal received one administration and the follow-up period was 2 months. Each sheep in these two treatment groups received the prostate implant by a single dose of 250 mg or 500 mg of 2-hydroxyflutamide. The control group of five animals received the ceramic based implant without 2-hydroxyflutamide. The implant drug delivery system was inserted into one location of the prostate tissue through rectum by using needles and ultrasound guidance. The animals were under general anaesthesia during the insertion procedure. The needle (15 cm long sized 13 Gauge) was inserted into the prepared rectum through the rectal and abdominal wall and positioned in the prostate tissue. The implant dose was given into the prostate as one constrained volume of approximately 2 and 4 ml in each prostate globe.

For the manufacturing of the implant compositions, the powder was densified together with the 2-hydroxyflutamide using cold isostatic pressing. Calcium-sulphate hemi-hydrate was first uniaxially pressed to loosely pressed rod shaped samples with low pressure. The samples were wetted, placed in balloons and immediately exposed to an isostatic pressure of 200 MPa for 30 minutes. Further sterile water was added afterwards to reach full hydration. For each gram of sulphate a total of 0.19 g of water was used in total. Samples containing (50 and) 100 mg of 2-hydroxyflutamide in 1.0 g of calcium sulphate were prepared.

The compacted samples were crushed to grains of size 125-500 µm using a Fritsch Pulverisette type 1, and mixed with non-hydrated and milled calcium sulphate powder in proportions 1:2 by weight. For the animal tests batches of powder containing 2.5 g of the crushed grains and 5.0 g of non-compacted calcium sulphate hemi-hydrate were prepared.

The powder was mixed with a aqueous liquid of sterile water and 1% of methylcellulose and 1% of acetic acid was prepared. Each such batch of powder was mixed with 3.5 ml of aqueous liquid and mixed to a paste.

The plasma concentration of 2-hydroxyflutamide was quantified with a validated HPLC-MS-MS chromatography method.

Results—Compacted Calcium Sulphate

The concentration of 2-hydroxyflutamide in plasma as a function of time is illustrated in FIG. 6 for the compacted samples. For the compositions used the amount of 2-hydroxyflutamide was reduced.

It is evident that the release rate of the drug is further reduced with the densified formulation as the half-life of the declining plasma concentration is xx days. This is a prolongation of the in vivo drug release by 5 times compared to the non-densified formulation used in dogs. It is approximated from pharmacokinetic models that about 40% of the dose has been released at day 25 and therefore the local drug release will proceed and generate local concentration that will result in a pharmacological and clinical effect. It is also evident that the in vitro release method also predicts the in vivo drug release profile with high accuracy.

After termination of the animals after 50 days, the implants were almost entirely disappeared.

It was also clear that the volume of the prostate tissue was significantly reduced in male sheep that were given the controlled release implant containing the pharmacologically active 2-hydroxyflutamide. The male sheep that were given a formulation without the pharmacologically active 2-hydroxyflutamide, there was no effect on the volume of the prostate gland. The plasma concentrations of 2-hydroxyflutamide was low and accordingly no side effect related to the active drugs was observed.

Example 9

This example illustrates further the effect of compaction on the release rate of 2-hydroxy-flutamide from calcium sulphate based formulations. Structures with compacted high-density calcium sulphate grains containing entrapped 2-hydroxy-flutamide are presented.

FIG. 7 shows release rates from compacted grains containing 100 mg or 50 mg of 2-hydroxyflutamide per g of calcium sulphate hemi hydrate of starting powder. Either the grains are incorporated in a cured calcium sulphate-water paste (X, Y) or the grains alone are tested in a water based in vitro release test set-up (Z).

The compacted grains were manufactured as in Example 6 using isostatic pressing at 200 MPa followed by crushing of the densified material. The grains were sieved to the size span of 125-500 microns, and they contained 50 mg or 100 mg of 2-hydroxyflutamide per gram of calcium-sulphate hemi-hydrate, also as in example 6.

Batches of powder containing 2.5 g of the crushed grains (with 50 or 100 mg/g of 2-hydroxyflutamide) and 5.0 g of non-compacted calcium sulphate hemi-hydrate (without 2-hydroxyflutamide) were prepared. The powder was mixed with 3.5 ml of water containing 1% of acetic acid and 1% of methyl cellulose, forming a paste which was split in 5 separate units and left to cure. Thus each sample contained 0.5 g of densified grains and 1.0 g of non-densified calcium sulphate. The samples prepared from the grains with 100 mg/g of 2-hydroxyflutamide thus contain a total of 50 mg of 2-hydroxyflutamide; and the samples prepared with grains containing 50 mg/g hold a total of 25 mg of 2-hydroxyflutamide.

The samples selected for release tests are:

X: Grains of densified calcium sulphate with 50 mg/g of 2-hydroxyflutamide in a matrix of hydrated calcium sulphate paste.

Y: Grains of densified calcium sulphate with 100 mg/g of 2-hydroxyflutamide in a matrix of hydrated calcium sulphate paste.

Z: The compacted grains with 100 mg/g 2-hydroxyflutamide analysed alone, without being embedded in a ceramic matrix). A total of 0.5 g of the grains (thus containing 50 mg of 2-hydroxyflutamide) was tested.

For the in vitro release tests, the samples were placed in glass containers containing 100 ml of sterile NaCl saline solution (9 mg/ml) incubated in a water bath at 37° C. for up to 30 days. At predetermined intervals 4 ml of the solution was collected, and replaced with 4 ml of fresh sterile saline.

The saline samples were quantified regarding the concentration of 2-hydroxyflutamide by using an analytical LC-MS-MS chromatography method.

Results

It is seen in FIG. 7 that all the samples release 2-hydroxyflutamide at a rate which is initially higher and which falls to a lower level after the first 15-20 days. Still after 30 days a considerable part of the 2-hydroxyflutamide still remains in the ceramic carrier. The release rate characteristics is roughly similar for both the two-phase samples, although the sample entrapping the higher concentration of 2-hydroxyflutamide has released a lower share of the total drug load. The free grains release at a higher rate initially during the first 5-10 days; thereafter the rate is about equal to rate of the composite samples up to about 30 days. It is thus illustrated that the cured matrix surrounding the densified grains reduced the release rate during the first about 10 days, and perhaps also in a perspective of above 30 days.

The invention claimed is:

1. A method for preparing a ceramic composition for controlled release of a pharmaceutically active substance, comprising the steps of:
   i) mixing one or more hydratable and bioresorbable ceramics with one or more pharmaceutically active substances,
   ii) densifying the mixture obtained in i) by applying an external pressure, and
   iii) hydrating the ceramic during the densification in step ii) by adding water to the resulting mixture from step i) in an amount corresponding to from about 20% to about 120% of the stoichiometric amount necessary to fully hydrate the one or more ceramics, whereby a highly densified and at least partly hydrated ceramic is obtained with a porosity of below 7%, wherein the applied external pressure in step ii) is of at least 20 MPa for at least 10 minutes.

2. The method according to claim 1, wherein the water is added prior to densification.

3. The method according to claim 1, wherein the one or more ceramics are at the most partly hydrated prior to densification in step ii).

4. The method according to claim 1, wherein the water is added at the time of the densification in step ii).

5. The method according to claim 1, wherein the amount of water added corresponds to from about 20% to at most 110% of the amount corresponding to the stoichiometric amount necessary to fully hydrate the one or more ceramics.

6. The method according to claim 1, wherein the amount of water added corresponds to at least 30% to about 120% of the amount corresponding to the stoichiometric amount necessary to fully hydrate the one or more ceramics.

7. The method according to claim 1, wherein the amount of water added is in a range corresponding to from 90% to 110% of the amount corresponding to the stoichiometric amount necessary to fully hydrate the one or more ceramics.

8. The method according to claim 1, wherein the water added in step iii) is comprised in an aqueous medium.

9. The method according to claim 8, wherein the aqueous medium comprises an organic acid comprising a carboxylic acid group.

10. The method according to claim 8, wherein the aqueous medium delays curing of the one or more hydratable and bioresorbable ceramics.

11. The method according to claim 1, wherein the mixture of step i) or the water in step iii), or both the mixture of step i) and the water in step iii), comprises one or more other active substances, additives or other pharmaceutically acceptable excipients to modify the micro-structure and the release rate.

12. The method according to claim 2, wherein the addition of the water takes place at the most 2 hours before densification.

13. The method according to claim 1, wherein the external pressure is provided by uniaxial or isostatic pressing, or by both uniaxial and isostatic pressing.

14. The method according to claim 1, further comprising a step iv) of post-hydrating the densified and at least partly hydrated ceramic.

15. The method according to claim 14, wherein the total amount of water used to hydrate the one or more ceramics essentially corresponds to the stoichiometric amount necessary to fully hydrate the one or more hydratable and bioresorbable ceramics ±10%.

16. The method according to claim 1, comprising a step prior to step i) of reducing the mean particle size of the hydratable and bioresorbable ceramic.

17. The method according to claim 16, wherein the mean particle size of the hydratable and bioresorbable ceramic is reduced to at the most 10 μm.

18. The method according to claim 16, wherein the reduction in particle size is performed by milling the one or more hydratable and bioresorbable ceramics.

19. The method according to claim 1, further comprising a step of granulating the one or more hydratable and bioresorbable ceramics prior to step i).

20. The method according claim 1, further comprising a step of shaping the mixture obtained in step i), prior to subjecting the mixture to step ii).

21. The method according to claim 20, wherein the mixture obtained in step i) is granulated by freeze granulation, wet granulation, or dry granulation.

22. The method according to claim 11, wherein the one or more pharmaceutically acceptable excipients are added in step i).

23. The method according to claim 1, wherein the highly densified and at least partly hydrated ceramic obtained has a porosity of at the most 5%.

24. The method according to claim 1, wherein the highly densified and at least partly hydrated ceramic obtained has a pore size of at the most 100 nm.

25. The method according to claim 1, wherein the one or more hydratable and bioresorbable ceramics are a non-hydrated, hydrated, semi-hydrated or partly hydrated ceramic selected from the group consisting of calcium sulphate; calcium phosphate; calcium carbonate; calcium fluoride; calcium silicate; magnesium sulphate; magnesium phosphate; magnesium carbonate; magnesium fluoride; magnesium silicate; barium sulphate; barium phosphate; barium carbonate; barium fluoride; and barium silicate; and mixtures thereof.

26. The method according to claim 1, wherein the one or more hydratable and bioresorbable ceramics are non-hydrated, hydrated, semi-hydrated or partly hydrated calcium sulphate, or mixtures thereof.

27. The method according to claim 1, wherein the hydratable and bioresorbable ceramic is calcium-sulfate hemi-hydrate and the total amount of water used to hydrate the ceramic during employment of external pressure, or both and after employment of external pressure is at the most 1.5±0.015 molar equivalents of water.

28. The method according to claim 1, wherein the hydratable and bioresorbable ceramic is calcium-sulfate hemi-hydrate and the total amount of water employed in step iii) is at the most 1.5 molar equivalents of water.

29. The method according to claim 1, wherein the one or more pharmaceutically active substances are dispersed in the highly densified and at least partly hydrated ceramic.

30. The method according to claim 1, wherein the one or more pharmaceutically active substances are homogeneously dispersed in the highly densified and at least partly hydrated ceramic.

31. The method according to claim 1, wherein the one or more highly densified and at least partly hydrated ceramics wholly or at least partly encapsulate the one or more pharmaceutically active substances.

32. The method according to claim 1, wherein the one or more pharmaceutically active substances are sorbed on the one or more hydratable and bioresorbable ceramics prior to step ii) and iii).

33. The method according to claim 1, wherein the one or more pharmaceutically active substances employed in step i) are an active substance suitable for use in a prostate related disease or condition.

34. The method according to claim 33, wherein the one or more pharmaceutically active substances is an androgen, an anti-androgen, an oestrogen, an anti-oestrogen, a gestagen, an anti-gestagen, an oligonucleotide, a progestagen, a gonadotropin-releasing hormone, a gonadotropin inhibitor, an adrenal and/or prostate enzyme inhibitor, a membrane efflux and/or membrane transport protein, an immune system modulator, an angiogenesis inhibitor, or combinations thereof.

35. The method of claim 34, wherein the one or more pharmaceutically active substances is an anti-androgen.

36. The method according to claim 1, wherein the pharmaceutically active substance is a combination of an anti-androgen and a gonadotropin-releasing hormone.

37. The method according to claim 1, wherein the one or more pharmaceutically active substances is flutamide or hydroxyflutamide, or a combination thereof.

38. A method for the preparation of a pharmaceutical composition comprising mixing a highly densified and at least partly hydrated ceramic obtained as defined in claim 1 together with one or more pharmaceutically acceptable excipients.

39. The method of claim 23, wherein the highly densified and at least partly hydrated ceramic has a porosity of at the most 1%.

40. The method of claim 1, wherein the pharmaceutically active substance is a therapeutically active substance.

41. The method of claim 1, wherein the pharmaceutically active substance is prophylactically active substance.

42. The method of claim 1, wherein the pharmaceutically active substance is diagnostically active substance.

43. The method according to claim 35, wherein the anti-androgen is flutamide, hydroxy-flutamide, cyproteron, nilutamide or bicalutamide or a combination thereof.

44. The method of claim 1, wherein the load of the pharmaceutically active substance in the highly densified and at least partly hydrated ceramic is at the most 50% w/w.

45. The method of claim 1, wherein the highly densified and at least partly hydrated ceramic is obtained in a particulate form.

46. The method of claim 1, wherein the one or more hydratable and bioresorbable ceramics in step i) are in the form of a powder.

* * * * *